United States Patent

Plant Pat. 3,974
Patented Nov. 16, 1976

1

3,974

DWARF SPUR TYPE RED DELICIOUS APPLE TREE

Jack D. Slusarenko, Rte. 2, Box 355,
Milton-Freewater, Oreg. 97862

Filed Sept. 29, 1975, Ser. No. 617,450
Int. Cl.[2] A01H 5/03
U.S. Cl. Plt.—35 1 Claim

ABSTRACT OF THE DISCLOSURE

As a mutation of Red Delicious, a new apple tree is disclosed which is characterized by its dwarf size, its compact form, and its stiff and rigid branches.

DESCRIPTION

The present invention relates to a new and distinct variety of apple tree which was discovered by me as a bud mutation dwarf during the supervision of my cultivated apple orchard located near Milton-Freewater, Oreg.

The apple tree which is the subject of my discovery was obtained from the same source and was planted at the same time and under identical conditions of soil as were its companion trees in a ten acre orchard. All of the trees were of the Bisbee strain of "Starkrimson Delicious," a patented variety of spur-type Red Delicious apple tree characterized normally by its large size.

During its growth, my new variety of apple tree received the same care, the same amount of water, the same amount and kind of fertilizer, and the same cultivation as did its companion trees.

As it continued to grow, I noted during my periodic orchard inspections that it differed markedly in its growth characteristics from its companion trees. Whereas its companion trees rapidly attained the large size characteristic of Red Delicious apple trees of this class, my new dwarf apple tree had a sharply reduced rate of growth. After several years, it had attained a size only about three fifths the size of its companion trees.

Nevertheless its fruiting characteristics were the same as those of its companion trees. The fruit set at the same time and developed at the same rate, well distributed throughout the tree. The fruit grew to the same ultimate size. It had the same color. It looked and tasted the same. However, due to its small size, the tree bore only about two-thirds the crop borne by its companion trees of normal size.

My newly discovered dwarf spur-type Red Delicious apple tree consequently demonstrates significant advantages. It needs no pruning. Its fruit can be picked from

2 the ground. The tree has stocky, compact rigid branches which need no limb support. It is adaptable for growth and cultivation in areas where space is limited, as in home gardens.

Recognizing the tree as a true dwarf, as opposed to a root-pruned dwarf, I asexually reproduced my new variety in my orchard at Milton-Freewater, Oreg., and its outstanding and distinctive characteristics appear to be permanent.

Figure 1:
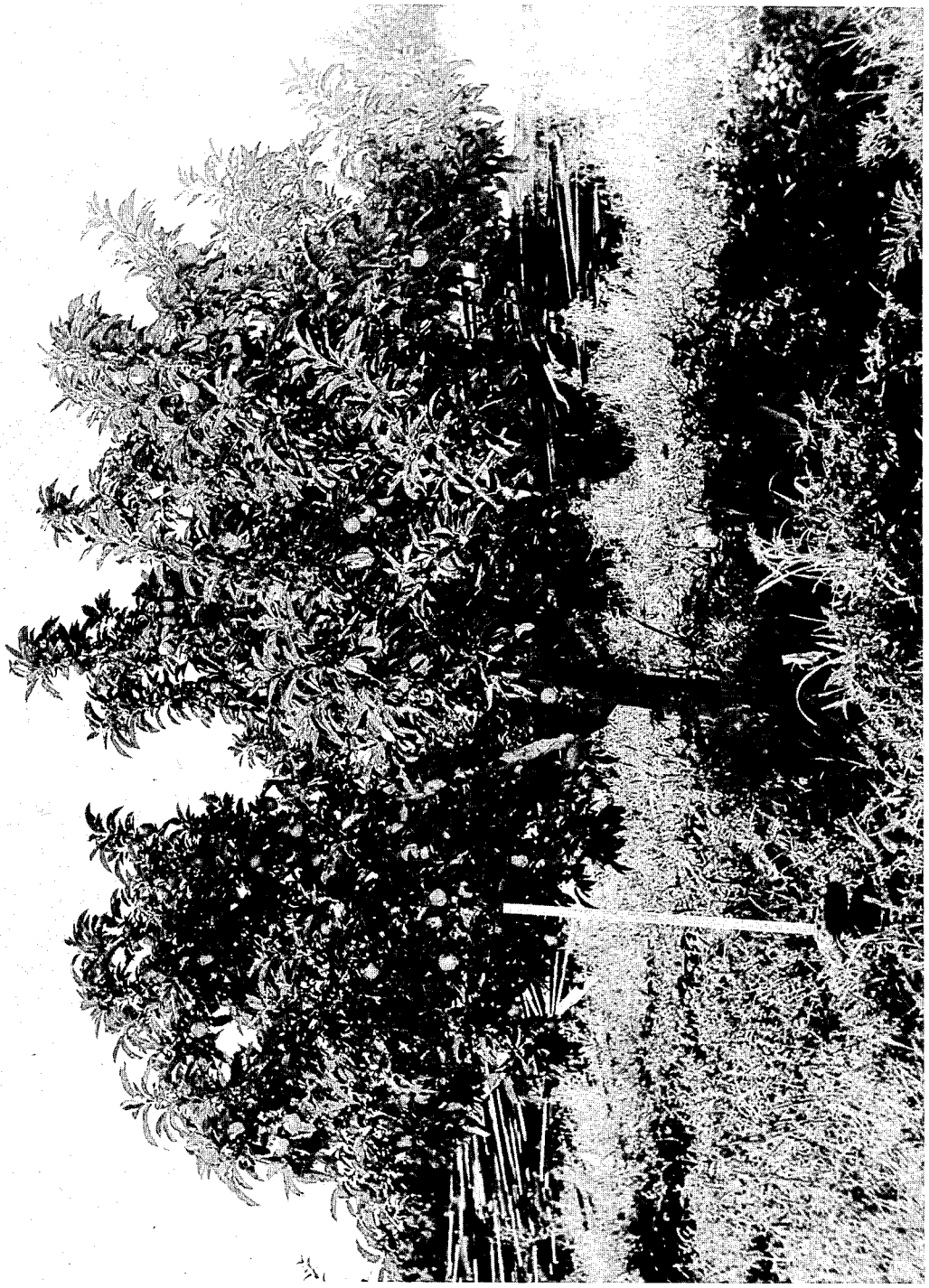
FIG. 1 is a photograph of my new apple tree in its entirety.
Figure 2:
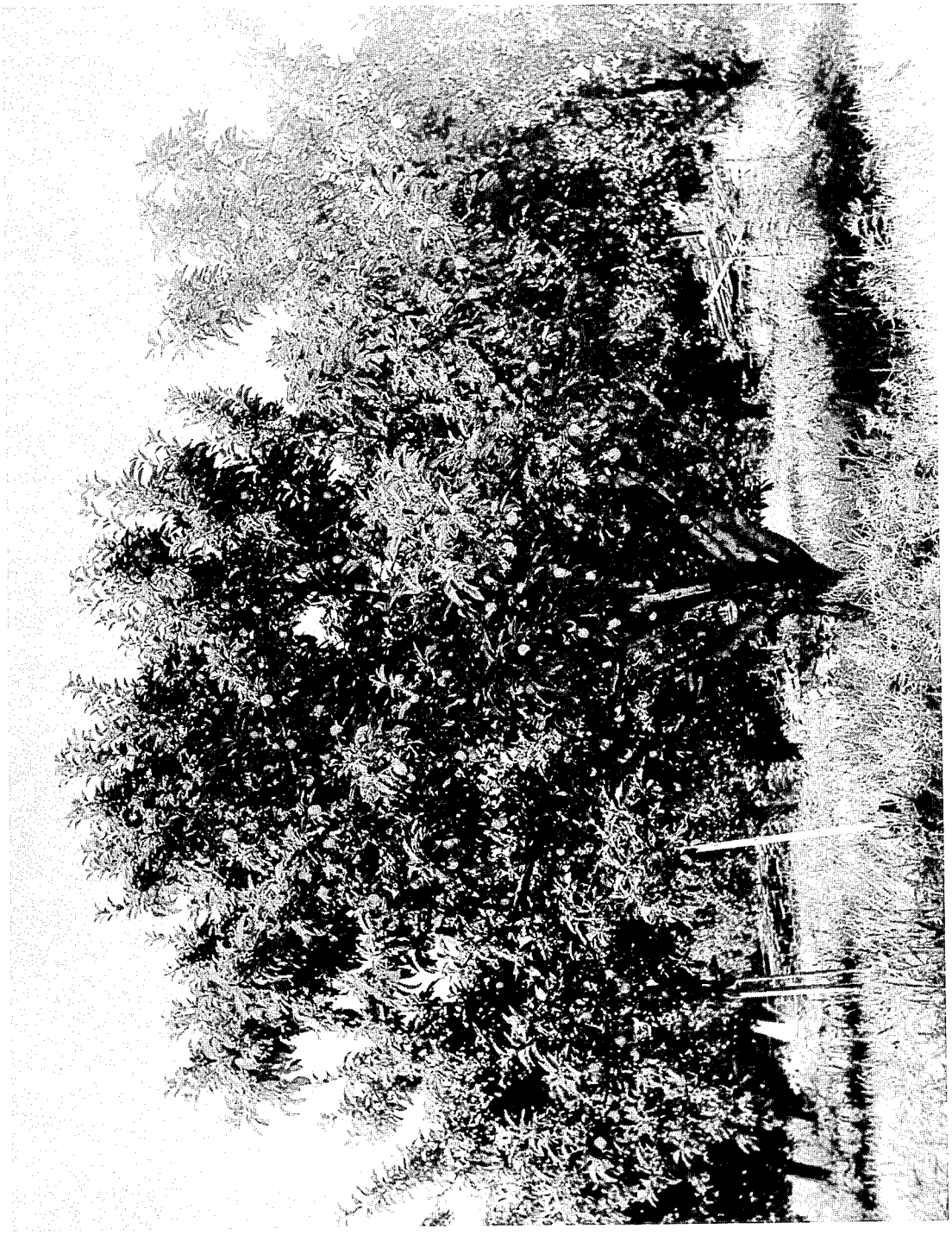
FIG. 2 is a photograph of one of the normal companion apple trees planted adjacent to and at the same time as my new apple tree.
Figures 3, 4:
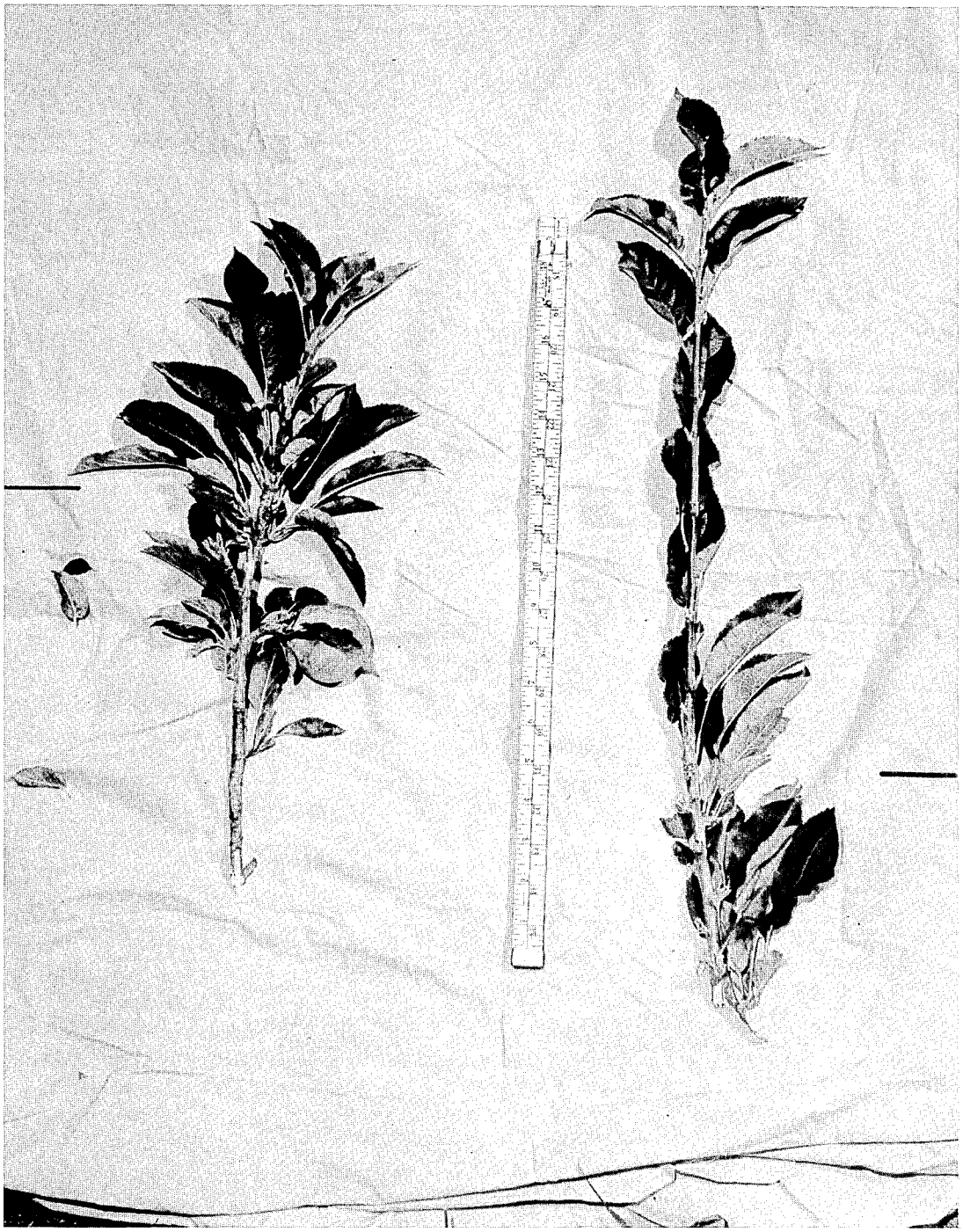
FIG. 3 is a photograph of a branch cut from my new apple tree with some of the leaves removed to reveal the bud, the new growth extension being above the reference line at the bud location.
FIG. 4 is a photograph of a branch cut for purposes of comparison from one of the companion trees of normal size planted adjacent to, and at the same time, as my new variety of apple tree, with some of the leaves removed to reveal the bud, the new growth extension being above the reference line at the bud location.

Summarizing the characteristics of my new apple tree:

Tree: Small; dwarf; compact form. Ultimate maximum height when 18 years old and fully grown, nine feet; spread eleven feet. Adjacent normal Bisbee strain reference variety of Red Delicious apple tree, ultimate maximum height when 18 years old and fully grown, eighteen feet; spread fifteen feet.

Roots: Identical root structure to the adjacent standard spur-type Red Delicious apple trees.

Branches: Stiff and rigid.

Flowers and leaves: Identical to the adjacent standard spur-type Red Delicious apple trees.

Fruit: Identical in size, shape, taste and color to, and matures at the same time as, the fruit of the adjacent standard spur-type Red Delicious apple trees.

I claim:

1. A new and distinct variety of apple tree, substantially as herein shown and described, characterized particularly as to novelty by the dwarf nature of its growth and characteristics, its compact growth structure, and its stiff and rigid branches.

No references cited.

ROBERT E. BAGWILL, Primary Examiner